United States Patent [19]
Hurwitz et al.

[11] Patent Number: 5,825,030
[45] Date of Patent: Oct. 20, 1998

[54] SHAPING NEUTRON ENERGIES TO ACHIEVE SENSITIVITY AND UNIFORMITY OF BULK MATERIAL ANALYSIS

[75] Inventors: Michael J. Hurwitz; Raymond J. Proctor; Siaka Yusuf, all of San Diego, Calif.

[73] Assignee: Gamma-Metrics, San Diego, Calif.

[21] Appl. No.: 822,075

[22] Filed: Mar. 20, 1997

[51] Int. Cl.⁶ .................................................. G01N 23/222
[52] U.S. Cl. .................................... 250/358.1; 250/359.1; 376/159
[58] Field of Search ............................ 250/358.1, 359.1, 250/390.04, 393, 394; 376/153, 156, 158, 159

[56] References Cited

U.S. PATENT DOCUMENTS

| | | |
|---|---|---|
| 3,053,388 | 9/1962 | Tittle . |
| 3,124,679 | 3/1964 | Tittman et al. . |
| 3,146,349 | 8/1964 | Jordan . |
| 3,278,747 | 10/1966 | Ohmart . |
| 3,631,247 | 12/1971 | Barton, Jr. . |
| 3,794,843 | 2/1974 | Chen . |
| 3,881,110 | 4/1975 | Hounsfield et al. . |

(List continued on next page.)

FOREIGN PATENT DOCUMENTS

| | | |
|---|---|---|
| 747312 | 5/1970 | Belgium . |
| 2066233 | 1/1992 | Canada . |
| 633467 | 1/1995 | European Pat. Off. . |
| 2613700 | 10/1977 | Germany ........................... 250/390.04 |
| 984491 | 12/1982 | U.S.S.R. ............................ 250/390.04 |

OTHER PUBLICATIONS

Strahlenther Onkol, vol. 165, (1989), pp. 87–90, Less et al.
Nuclear Instruments and Methods, vol. 73, (1969), pp. 13–33, Krinniger er al.
LA–6788–PR, (Jun. 1977), Sopir, pp. 1–54.
"MCNP—A General Monte Carlo Code for Neutron and Photon Transport" Version 3A, Sep. 1986, pp. iii, iv, vii, and 35–38.
English Translation of French Patent Application No. 90 09505 filed Jul. 15, 1990 corresponding to International Patent Application No. PCT/FR91/00498 filed Jun. 21, 1991.

*Primary Examiner*—Edward J. Glick
*Assistant Examiner*—Darren M. Jiron
*Attorney, Agent, or Firm*—Edward W. Callan

[57] ABSTRACT

In a bulk material analyzer in which bulk material is received in an activation region between a pair of neutron sources laterally disposed on one side of the activation region for emitting neutrons for bombarding the bulk material within the activation region to cause gamma-rays to be emitted from the bombarded bulk material and a pair of gamma-ray detectors laterally disposed on an opposite side of the activation region for detecting gamma-rays emitted from the bulk material, and in which a neutron moderator is disposed between the neutron sources and the activation region for reducing the velocity of the emitted neutrons such that the neutrons entering the activation region include thermal neutrons and faster neutrons, the uniformity of sensitivity of the bulk material analyzer to materials at different positions in a sample of the bulk material being analyzed is enhanced by controlling the proportions of thermal neutron at different positions within the sample being analyzed. A neutron absorber disposed close to the one side of the activation region reduces the proportion of thermal neutrons that enter the activation region from the one side of the activation region. A neutron reflector disposed on the opposite side of the activation region at least as close to the activation region as the gamma-ray detector(s) reflects neutrons into the activation region for bombarding bulk material within the activation region. In some embodiments, the neutron absorber and/or the neutron reflector are adjustable; and the disposition of the neutron sources also is adjustable for also adjusting the proportion of the thermal neutrons that enter the activation region from the one side of the activation region.

23 Claims, 3 Drawing Sheets

U.S. PATENT DOCUMENTS

| | | |
|---|---|---|
| 3,889,112 | 6/1975 | Holmes et al. . |
| 4,028,267 | 6/1977 | Christell et al. . |
| 4,041,315 | 8/1977 | Hounsfield . |
| 4,314,155 | 2/1982 | Sowerby . |
| 4,582,992 | 4/1986 | Atwell et al. . |
| 4,672,648 | 6/1987 | Mattson et al. . |
| 4,682,043 | 7/1987 | Marshall . |
| 4,809,172 | 2/1989 | Hopkinson et al. . |
| 5,076,502 | 12/1991 | Kitaguchi et al. . |
| 5,098,640 | 3/1992 | Gozani et al. . |
| 5,124,554 | 6/1992 | Fowler er al. . |
| 5,144,140 | 9/1992 | Allyson et al. . |
| 5,153,439 | 10/1992 | Gozani et al. . |
| 5,162,095 | 11/1992 | Alegre et al. . |
| 5,162,096 | 11/1992 | Gozani . |
| 5,396,071 | 3/1995 | Atwell et al. ................ 250/358.1 |
| 5,732,115 | 3/1998 | Atwell et al. ................ 376/159 |

SHAPING NEUTRON ENERGIES TO ACHIEVE SENSITIVITY AND UNIFORMITY OF BULK MATERIAL ANALYSIS

BACKGROUND OF THE INVENTION

The present invention generally pertains to bulk material analyzers and is particularly directed to improving measurement accuracy by enhancing the uniformity of sensitivity to materials at different positions in a sample analyzed by a bulk material analyzer of the type in which the bulk material is bombarded by neutrons within an activation region.

Bulk material analyzers are used to measure the elemental content of bulk materials. One type of bulk material analyzer includes one or more neutron sources and one or more gamma-ray detectors. When bulk material within an activation region between at least one neutron source disposed on one side of the activation region and at least one gamma-ray detector disposed on an opposite side of the activation region opposite from the one side is bombarded by neutrons, secondary emissions of gamma-rays are produced from the bombarded bulk material and detected by the gamma-ray detector(s). The gamma-ray detector(s) produce signals which are processed to provide an indication of the elemental content of the bulk material. Different characteristic gamma-ray energy spectra are produced from different elements in the bulk material. By processing detected signals that are indicative of the gamma-ray spectrum, a measurement is provided of the quantitative elemental content of the bulk material. This measurement process is known in the art as prompt gamma-ray neutron activation analysis (PGNAA).

Gamma rays are emitted from almost all elements within a bulk material when such elements capture neutrons. In order for such capture to occur the neutrons must be in thermal equilibrium with the surrounding material. When neutrons are emitted from a neutron source their velocity is so fast that they are not in thermal equilibrium with the surrounding material. Therefore, a neutron moderator is disposed about the neutron source(s) and the activation region for reducing the velocity of the emitted neutrons such that most of the neutrons entering the activation region have been slowed to such a velocity as to be in thermal equilibrium with the surrounding material. Neutrons moving at such a velocity as to be in thermal equilibrium with the surrounding material are slow neutrons that are referred to as thermal neutrons. Thermal neutrons move at such a velocity as to have an energy of less than approximately 0.5 eV. Neutrons moving at such a velocity as to have an energy in excess of 500 keV are referred to as fast neutrons; and neutrons having a velocity within a range of from 0.5 eV to 500 keV are referred to as epithermal neutrons. Herein, neutrons that are moving faster than thermal neutrons are referred to as "faster neutrons". A neutron moderator is a material that efficiently reduces the velocity of interacting neutrons to a few thousand meters per second. If a large thickness of the moderator is necessary to slow down as many neutrons as possible, the material should also have a low neutron-absorption characteristic. For small thicknesses, a more neutron-absorbing material may be used. Examples of neutron moderators include materials that contain low-atomic-number elements, such as Hydrogen, Deuterium, Beryllium, Carbon and Oxygen. Hydrogen is the best moderator, but it is partially neutron-absorbing and therefore is used in only small thicknesses to moderate neutrons. Popular neutron moderators include graphite and heavy water. The term "neutron moderator" is used herein to refer to materials that are primarily neutron moderating and not to other materials having neutron-moderating characteristics that are merely secondary to some other characteristic that motivates the use of such other materials.

European Patent Application Publication 0 633 467 A2 describes a bulk material analyzer in which measurement accuracy is improved by enhancing the spatial uniformity of response by the gamma-ray detector(s) to gamma-ray emission from different areas of a cross-sectional profile of an activation region within a passageway defined by container surfaces for enabling bulk material to be transported through the activation by a conveyor belt. The spatial uniformity of response is enhanced by disposing neutron moderators of selected thicknesses adjacent various portions of the activation-region-defining surfaces of the container that are at and lateral to one side and another opposite side of the activation region at which the neutron source(s) and the gamma-ray detector(s) are respectively disposed, for channeling and reflecting neutrons into the activation region. In an embodiment in which a lower portion of the passageway-defining surfaces define a trough having upwardly extended sides adjacent the activation region for cradling the conveyor belt, a neutron moderator is disposed adjacent the sides of the trough for channeling and reflecting the neutrons into the activation region. The respective thicknesses of the neutron moderating material disposed adjacent various portions of the activation-region defining surfaces of the container are determined for a sample of a given average profile within an activation region of given dimensions by computer-aided modeling in accordance a technique described in a manual entitled "MCNP—A General Monte Carlo Code for Neutron and Photon Transport" published by the Radiation Shielding Information Center, P.O. Box 2008, Oak Ridge, Tenn. 37831. Such computer-aided modeling also takes into consideration attenuation of the gamma rays by the neutron moderating material disposed between the sampled bulk material and the detectors, by gamma-ray attenuating material variably disposed over the detector(s) and by the sampled bulk material itself Nonetheless, spatial uniformity of response by the gamma-ray detector(s) to gamma-ray emission from different areas of a cross-sectional profile of an activation region still might not be achieved when the sample has a high Hydrogen content (such as over 0.5 percent Hydrog,en by weight, which occurs when a material sample having a depth in a range of from approximately fifteen centimeters to twenty five centimeters has a moisture content in excess of five percent) and/or is of such thickness such that the detector(s) are more sensitive to materials at some positions within a sample analyzed by the bulk material analyzer than to the same materials at other positions within the sample. For example, when a sampled bulk material being transported through the activation region on a conveyor belt is deeper than in the average cross-sectional profile for which the respective thicknesses of the neutron moderator material adjacent various portions of the activation-region-defining surfaces of the container were determined, or when the sampled bulk material on the conveyor belt has a high moisture content, the detector(s) are more sensitive to materials that are positioned closer to where the thermal neutrons enter the activation region.

In analysis applications where the bulk material is grossly segregated in the activation region with layered materials of very different chemical compositions, the bulk material analyzer described in European Patent Application Publication 0 633 467 A2 does not produce a sufficiently uniform sensitivity to avoid analysis errors as the layer thicknesses and/or the chemical compositions of the layered material change. In particular, when the materials have changing moisture/Hydrogen contents and/or greatly changing bed depths in the activation region, there is considerable non-uniformity of sensitivity.

SUMMARY OF THE INVENTION

The present invention provides a bulk material analyzer in which measurement accuracy is improved by controlling the proportions of thermal neutron at different positions within the sample being analyzed in order to enhance the uniformity of sensitivity of the bulk material analyzer to materials at different positions in the sample.

The present invention provides a bulk material analyzer in which bulk material is received in an activation region between at least one neutron source and at least one gamma-ray detector, comprising a container having surfaces defining the activation region; and at least one neutron source disposed within the container on one side of the activation region for emitting neutrons that enter the activation region for bombarding bulk material within the activation region to cause ganmma-rays to be emitted from said bombarded bulk material; at least one gamma-ray detector disposed within the container on another side of the activation region opposite from the one side of the activation region for detecting gamma-rays emitted from said bombarded bulk material; a neutron moderator disposed between the neutron source(s) and the activation region for reducing the velocity of said emitted neutrons such that the neutrons entering the activation region include thermal neutrons and faster neutrons; and a neutron absorber disposed close to the one side of the activation region for reducing the proportion of thermal neutrons that enter the activation region from the one side of the activation region. A neutron absorber is a material that preferentially absorbs neutron, even in thin layers. Only thermal neutrons can be absorbed efficiently. Examples include materials that contain Boron or Lithium, such as a mixture of boron powder with polyethylene or paraffin wax. The term "neutron absorber" is used herein to refer to materials that are primarily neutron absorbing and not to other materials having neutron-absorbing characteristics that are merely secondary to some other characteristic that motivates the use of such other materials.

By reducing the proportion of thermal neutrons that enter the activation region from the one side of the activation region when the bulk material sample is thicker and/or of a high moisture (or high Hydrogen) content, a smaller proportion of thermal neutrons are captured by bulk material positioned closer to the one side of the activation region, while the greater number of thermal neutrons produced within the sample being analyzed by the neutron moderating effect of the thicker sample and/or the higher moisture content of the sample offset the effect of the reduced proportion of thermal neutrons entering the activation region from the one side of the activation region, to thereby enhance the uniformity of thermal-neutron flux density at different positions within the sample being analyzed.

There are two types of thermal neutrons to be found in the bulk material sample within the activation region, those transported into the sample from externally moderated faster neutrons and those created within the sample by the moderating effect of the sample upon faster neutrons. As the moisture/Hydrogen levels increase within a sample the externally produced thermal neutrons are more heavily absorbed and have limited penetration, whilst the internally thermalized neutrons have a more uniform spatial distribution. This combination of externally produced thermal neutrons and internally thermalized neutrons can be tailored to provide a desired thermal neutron flux distribution in the sample. This can be accomplished by adjusting the external neutron moderators, reflectors and absorbers. The desired thermal neutron flux distribution is normally selected to give thee best spatial uniformity of sensitivity.

The present invention also provides a method of enhancing uniformity of sensitivity of a bulk material analyzer to materials at different positions in a sample of bulk material received in an activation region between at least one neutron source disposed on one side of the activation region for emitting neutrons that enter the activation region for bombarding bulk material within the activation region to cause gamma-rays to be emitted from said bombarded bulk material, and at least one gamma-ray detector disposed on another side of the activation region opposite from the one side of the activation region for detecting gamma-rays emitted from said bombarded bulk material, wherein the bulk material analyzer includes a neutron moderator disposed between the neutron source(s) and the activation region for reducing the velocity of said emitted neutrons such that the neutrons entering the activation region include thermal neutrons and faster neutrons, the method comprising the step of:

(a) adjusting the proportion of thermal neutrons that enter the activation region from the one side of the activation region.

In another aspect, the present invention provides a method of enhancing uniformity of sensitivity of a bulk material analyzer to materials at different positions in a sample of bulk material received in an activation region between at least one neutron source disposed on one side of the activation region for emitting neutrons that enter the activation region for bombarding bulk material within the activation region to cause gamma-rays to be emitted from said bombarded bulk material, and at least one gamma-ray detector disposed on another side of the activation region opposite from the one side of the activation region for detecting gamma-rays emitted from said bombarded bulk material, wherein the bulk material analyzer includes a neutron moderator disposed between the neutron source(s) and the activation region for reducing the velocity of said emitted neutrons such that the neutrons entering the activation region include thermal neutrons and faster neutrons, the method being performed specifically for enhancing analysis by the bulk material analyzer of a batch of bulk material when the bulk material analyzer has not been adjusted to be uniformly sensitive to material at different positions in the samples of bulk material being analyzed and comprising at least one of the following steps:

(a) adjusting the proportion of thermal neutrons that enter the activation region from the one side of the activation region;

(b) adjusting the quantity of neutrons that enter the activation region from the other side of the activation region; and (c) adjusting the disposition of the bulk material sample in the activation region.

Additional features of the present invention are described in relation to the detailed description of the preferred embodiments.

DETAILED DESCRIPTION

Figure 1:
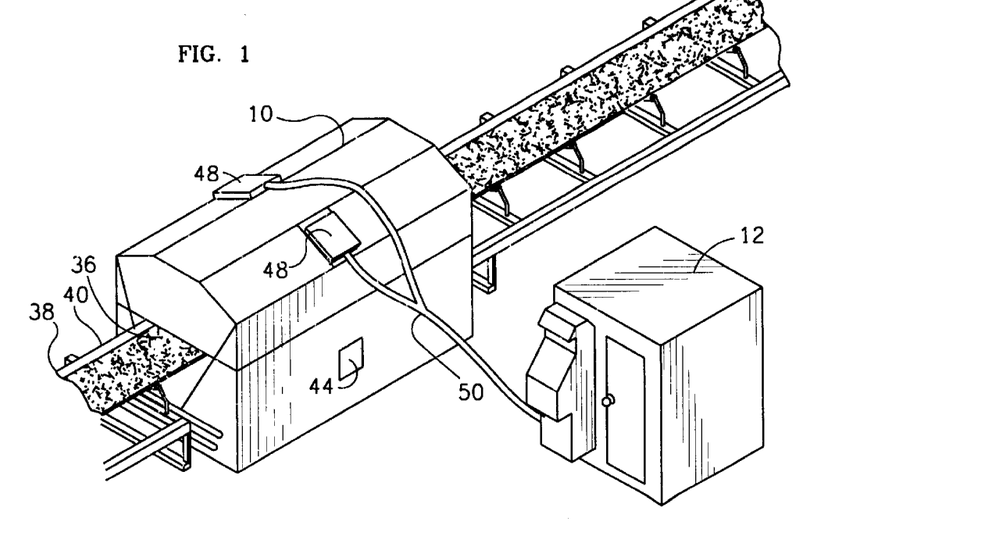
FIG. 1 is a perspective view illustrating a preferred embodiment of the bulk material analyzer of the present invention, in which a conveyor belt transports bulk material through the material analyzer assembly.
Figure 2:
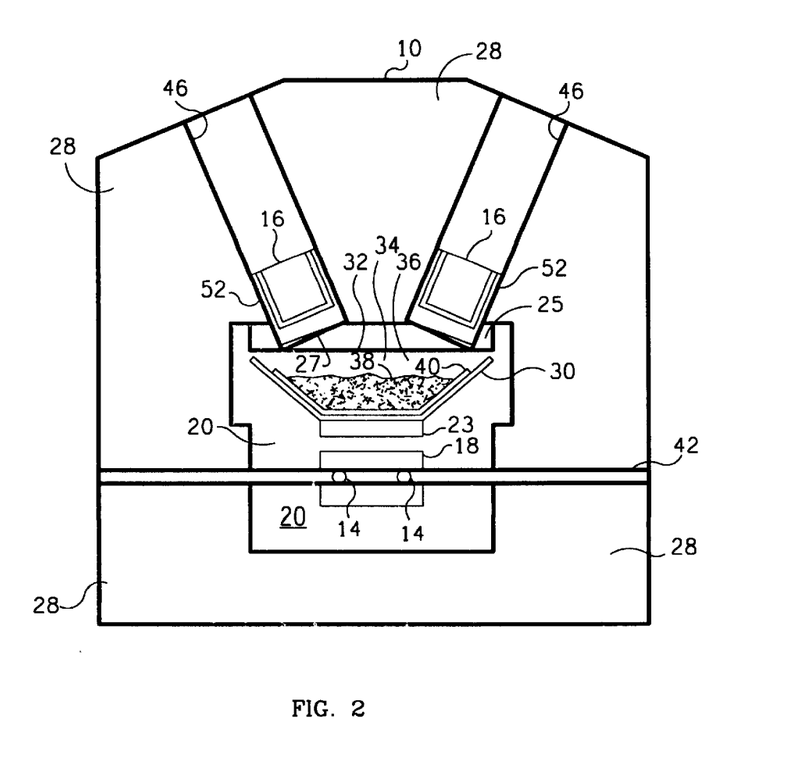
FIG. 2 is a diagram of a preferred embodiment of the portion of the bulk material analyzer adjacent the activation region, as viewed in the direction of the conveyor belt.

Referring to FIGS. 1 and 2, a preferred embodiment of a bulk material analyzer according to the present invention includes a container 10, a data processor (not shown) within a separate housing 12, a pair of neutron sources 14, a pair of gamma-ray detectors 16, a gamma-ray shield 18, a neutron moderator 20, a neutron absorber 23, a neutron reflector 25 and radiation shielding material 28. The neutron moderator 20 preferably is graphite. In alternative embodiments, the neutron moderator 20 may include separate sections of different neutron moderating materials, as described in European Patent Application Publication 0 633 467 A2.

The container 10 has interior surfaces 30, 32 defining an activation region 34 between the neutron sources 14 and the gamma-ray detectors 16. A lower portion of the passageway-defining surfaces 30, 32 defines a trough 30 having upwardly extended sides adjacent the activation region 34. The container surfaces 30, 32 further define a passageway 36 for enabling bulk material 38 to be transported through the activation region 34 on a conveyor belt 40.

The neutron sources 14 are disposed within the container 10 beneath the passageway 36 on one (the lower) side of the activation region 34 for emitting neutrons for bombarding bulk material 38 being transported on a conveyor belt 40 through the activation region 34 to cause gamma-rays to be emitted from the bombarded bulk material 38. The neutron sources 14 are inserted through a tubular neutron source cavity 42 in the container 10 into selected positions beneath the passageway 36, and are separated laterally on opposite sides of the longitudinal axis of the passageway 36. The neutron sources 14 are inserted into the neutron source cavity 42 through a door 44 in the container 10. Lateral separation of the neutron sources 14 suppresses the response of the gamma-ray detectors 16 to a given quantity of a given bulk material 38 located at the center of the activation region 34.

The gamma-ray detectors 16 are disposed within the container 10 above the passageway 36 on another (the upper) side of the activation region 34 opposite from the one side for detecting gamma-rays emitted from the bombarded bulk material 38. The gamma-ray detectors 16 are inserted through detector cavities 46 in the container 10 into selected positions above the passageway 36. The gamma-ray detectors 16 are inserted into the detector cavities 46 through hatches 48 in the container 10. Signals produced by the gamma-ray detectors 16 are provided by electrical cables 50 to the data processor within the housing 12.

The two gamma-ray detectors 16 are disposed toward opposite ends of the upper side of the activation region 34. Each detector 16 is skewed so that a portion of each detector 16 which is closer to the end of the upper side of the activation region toward which the detector 16 is disposed than to the center of the upper side, is disposed closer to a plane parallel to the upper side and passing through the center of the activation region 34 than is another portion of each detector 16 that is closer to the center of the upper side than to the end of the upper side toward which the detector 16 is disposed. Such skewing of the gamma-ray detectors 16 further enhances the response of the gamma-ray detectors 16 for a given quantity of a given bulk material 38 located near the lateral edges of the activation region 34, and also suppresses the response of the gamma-ray detectors 16 to the given quantity of the given bulk material 38 located at the center of the activation region 34.

In some embodiments, still additional suppression of the response of the gammaray detectors 16 to the given quantity of the given bulk material 38 located at the center of the activation region 34 may be provided when necessary by wedge-shaped spatial compensators 27, which are disposed over the ends of the gamma-ray detectors 16 that are adjacent the activation region 34.

In one embodiment, in which the spatial compensators 27 are primarily neutron moderating material, the spatial compensators 27 are disposed adjacent the upper side of the activation region 34 for reflecting neutrons toward the activation region 34 at a greater density toward opposite lateral ends of the upper side than toward the center of the upper side. The wedge-shaped spatial compensators 27 have a thickness that increases in a direction away from the center of the upper side of the activation region 34, as shown in FIG. 2.

In an alternative embodiment, the spatial compensators 27 are respectively disposed over the gamma-ray detectors 16 for gradually attenuating gamma-ray detection by the detectors 16 in accordance with proximity to the center of the upper side of the activation region 34, with the attenuation increasing in a direction toward the center of the upper side. In this alternative embodiment, the spatial compensators 27 have a thickness that decreases in a direction away from the center of the upper side of the activation region 34, which is the opposite from that which is shown in FIG. 2 for the neutron reflecting material wedges.

The number of neutron sources 14 and the number of ganmma-ray detectors 16 is dependent upon the width of the activation region 34, and may be increased beyond two neutron sources 14 and two gamma-ray detectors 16 as required to optimize the spatial uniformity of response by the gamma-ray detectors 16. The spatial uniformity of response also is dependent upon the cross-sectional profile of the bulk material 38 on the conveyor belt 40 within the activation region 34, as defined by the depth of the bulk material 38 at different lateral positions of a cross-section normal to the direction of movement of the conveyor belt 40, as shown in FIG. 2. Accordingly, the disposition of the neutron sources 14 within the neutron source cavity 42 and the disposition of the gamma-ray detectors 16 within detector cavities 46 may be adjusted in accordance with the cross-sectional profile of the bulk material 38 on the belt 40 within the activation region 34.

The gamma-ray shield 18 is a heavy metal, such as Bismuth, which is disposed within the container 10 about the neutron sources 14 for shielding the detectors 16 from gamma rays emitted from the neutron sources 14 so as to minimize detection by the detectors 16 of gamma rays from other than the bulk material 38 in the activation region 34.

A neutron shield 52 is disposed about each gamma-ray detector 16 for shielding the detectors 16 from stray neutrons so as to prevent detection by the detectors 16 of gamma rays secondarily emitted from within the gamma-ray detectors 16 as result of bombardment by neutrons of materials within the gamma-ray detectors 16.

The neutron moderator 20 is disposed between the neutron sources 14 and the activation region 34 for reducing the velocity of the neutrons emitted from the neutron sources 14 such that the neutrons entering the activation region include both thermal neutrons and faster neutrons. Reduction of neutron velocity enhances capture of the neutrons by the bulk material 38 so as to produce gamma-ray emission from the bulk material 38. The neutron moderator 20 also is disposed adjacent the upwardly extended sides of the trough 30 for channeling and reflecting neutrons into the activation region 34 to thereby enhance the response of the gamma-ray detectors 16 for a given quantity of a given bulk material 38 located near the lateral edges of the activation region 34.

The neutron absorber 23 is disposed between at least almost all of the neutron moderator 20 and the lower side of the activation region 34 for reducing the proportion of thermal neutrons that enter the activation region from the lower side of the activation region 34. Anything in excess of a small amount of neutron moderator 20 disposed between the neutron absorber 23 and the activation region 34 would negate the reduction in the proportion of thermal neutrons effected by the neutron absorber 23. Preferably, the neutron absorber is disposed about 2.5 centimeters below the lower side of the conveyor belt 40 beneath the trough 30. In an alternative embodiment, the neutron absorber 23 is included in the conveyor belt 40.

In an alternative embodiment (not shown), the portion of the bulk material analyzer shown in FIG. 2 is modified by omitting the neutron moderator 20 from the space directly between the gamma-ray shield 18 and the neutron absorber 23. The remainder of the neutron moderator 20 disposed adjacent the upwardly extended sides of the trough 30 and beneath and to the sides of the gamma-ray shield 18 still reduces the velocity of some of the neutrons before they enter the activation region 34. In this alternative embodiment, the neutron absorber 23 may be disposed closer to the neutron source(s) 14 than it 23 would be if the neutron moderator 20 was also disposed between the gamma-ray shield 18 and the neutron absorber 23.

The portion of the trough 30 adjacent the neutron moderator 20 and the neutron absorber 23 is made of a neutron transmissive material that enables the neutrons to diffuse into the activation region 34 from the neutron moderator 20 and the neutron absorber 23.

The neutron reflector 25 is disposed above the activation region 34 at least as close to the upper side of the activation region 34 as the gamma-ray detectors 16 for reflecting neutrons into the activation region 34 for bombarding bulk material 38 within the activation region to cause gamnma-rays to be emitted from the bombarded bulk material 38. The neutron reflector 25 is primarily neutron moderating material. Preferably, the neutron reflector 25 is a polyethylene sheet having a thickness in a range of approximately 1.3 to 5 centimeters depending upon the moisture content of the bulk material 38 being analyzed, and the neutron reflector 25 is disposed less than approximately 12.5 centimeters above the top of the bulk material 38 on the conveyor belt 40.

Figure 3:
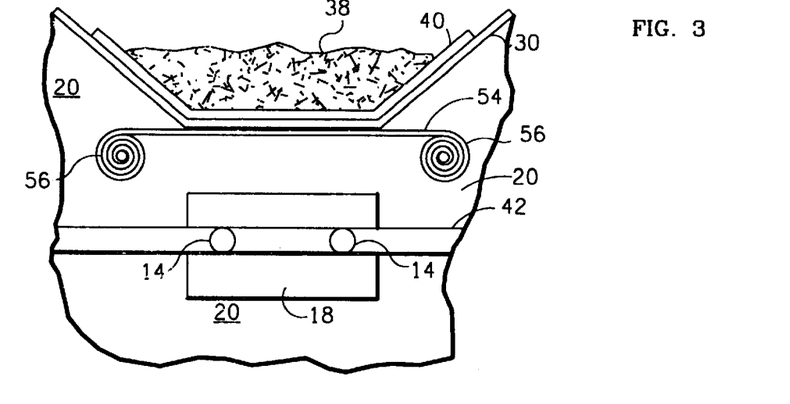
FIG. 3 is a diagram of an alternative preferred embodiment of the portion of the bulk material analyzer adjacent the activation region, as viewed in the direction of the conveyor belt, in which one embodiment of an adjustable neutron absorber is shown.

Referring to FIG. 3, an alternative preferred embodiment includes an adjustable neutron absorber in the form of a belt 54 having different concentrations of borated material (such as boron embedded in silicon rubber or polyester) in different segments of the belt. The belt 54 is wound onto a pair of reels 56 respectively disposed adjacent opposite ends of the lower side of the activation region 34 so that the portion of the belt 54 between the reels 56 is disposed between the neutron moderator 20 and the activation region 34. The respective concentrations of boron in the different segments enable the percentage of thermal neutrons that are absorbed in a single passage through the neutron absorber 54 to be adjusted from approximately zero to approximately one-hundred percent by disposing a selected segment of the belt 54 between the neutron moderator 20 and the activation region 34. In one example, one segments absorbs approximately zero percent of the thermal neutrons, a second segment absorbs forty percent of the thermal neutrons and a third segment absorbs approximately one-hundred percent of the thermal neutrons. The neutron absorber can be adjusted to adjust the proportion of thermal neutrons that enter the activation region 34 from the lower side of the activation region 34 by repositioning the belt 54 so that the segment providing the desired percentage of thermal-neutron absorption is disposed between the neutron moderator 20 and the activation region 34. In other respects the embodiment of FIG. 3 is the same as the embodiment of FIG. 2.

Figure 4:
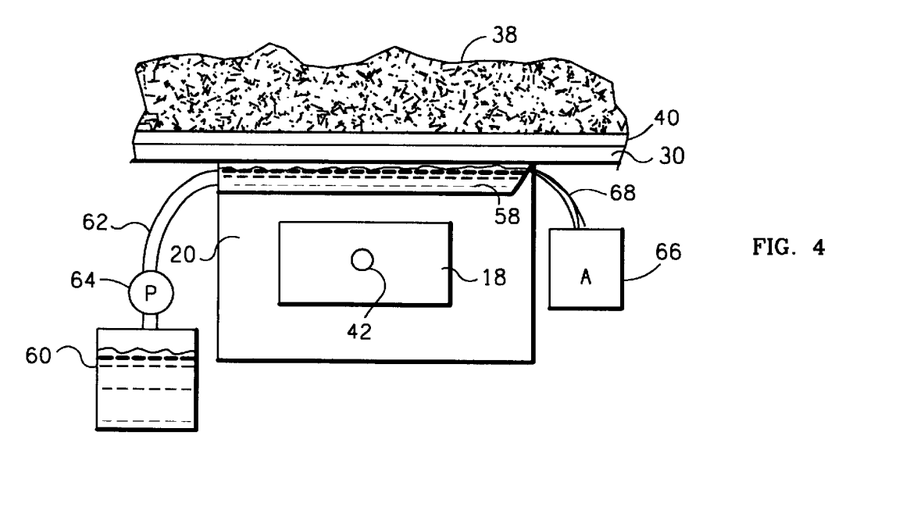
FIG. 4 is a diagram of another alternative preferred embodiment of the portion of the bulk material analyzer adjacent the activation region, as from one side of the conveyor belt, in which an alternative embodiment of an adjustable neutron absorber is shown.

Referring to FIG. 4, an alternative preferred embodiment includes an alternative adjustable neutron absorber in the form of a boric-acid-solution chamber 58 disposed between the neutron moderator 20 and the activation region 34. The boric acid solution is pumped into the chamber 58 from a tank 60 through a conduit 62 by a pump 64. An air tank 66 is connected to the chamber 58 by an air line 68 in order to maintain such pressure within the chamber 58 as to enable the level of the quantity of boric acid solution within the chamber 58 to be readily adjusted. The chamber 58 is slightly inclined from the horizontal to enable the boric acid solution to drain from the chamber 58 into the tank 60. The percentage of thermal neutrons that are absorbed is adjusted by adjusting the level of boric acid solution within the chamber 58. In other respects the embodiment of FIG. 4 is the same as the embodiment of FIG. 2.

Figure 5:
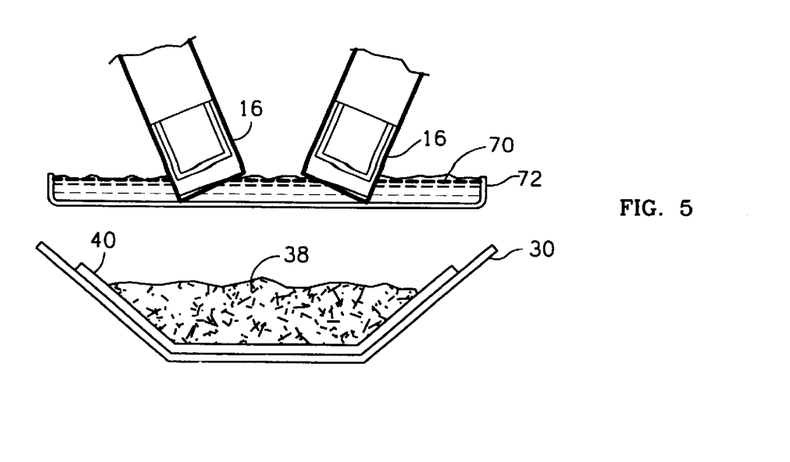
FIG. 5 is a diagram of yet another alternative preferred embodiment of the portion of the bulk material analyzer adjacent the activation region, as viewed in the direction of the conveyor belt, in which an adjustable neutron reflector disposed above the activation region is shown.

Referring to FIG. 5, yet another alternative preferred embodiment includes an adjustable neutron reflector in the form of a liquid neutron moderator/reflector 70 in a tank 72 of neutron moderating material disposed above the activation region 34 at least as close to the upper side of the activation region 34 as the gamma-ray detectors 16 for reflecting neutrons into the activation region 34 for bombarding bulk material 38 within the activation region to cause gamma-rays to be emitted from the bombarded bulk material 38. The liquid neutron moderator 70 is water or a liquid hydrocarbon, such as a paraffin oil, having a Hydrogen content greater than ten percent by weight or ninety grams/liter; and the tank 72 is made of polyethylene. The quantity of neutrons that are reflected by the neutron reflector 70, 72 to enter the activation region 34 from the upper side of the activation region 34 is adjusted by adjusting the quantity of liquid neutron moderator 70 in the tank 72. In other respects the embodiment of FIG. 5 is the same as the embodiment of FIG. 2.

Figure 6A:
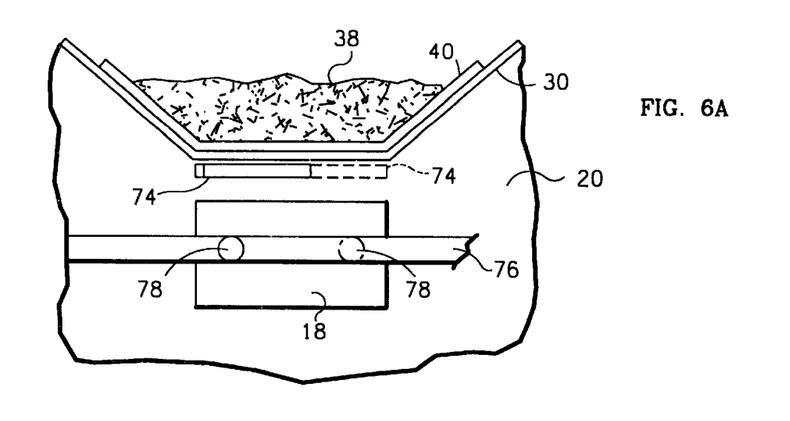
FIG. 6A is a diagram of still another alternative preferred embodiment of the portion of the bulk nmaterial analyzer adjacent the activation region, as viewed in the direction of the conveyor belt, in which an adjustable means for adjusting the proportion of the thermal neutrons that enter the activation region is shown.
Figure 6B:
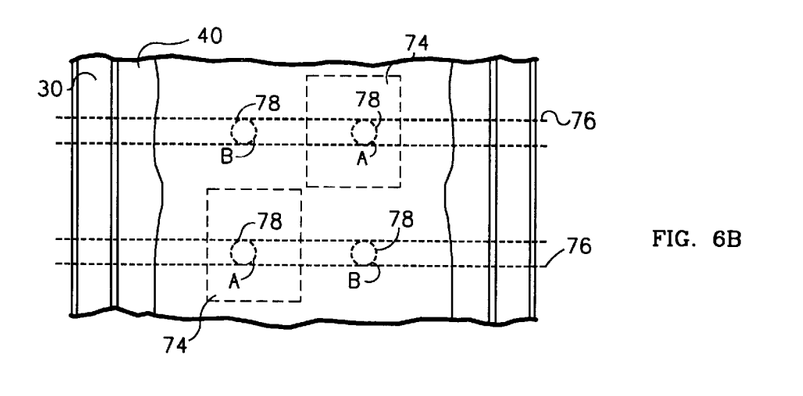
FIG. 6B is a diagram of the alternative preferred embodiment of the portion of the bulk material analyzer adjacent the activation region shown in FIG. 6A, as viewed from above the conveyor belt.

Referring to FIGS. 6A and 6B still another alternative preferred embodiment includes adjustable means for adjusting the proportion of thermal neutrons that enter the activation region 34 in the form of a pair of neutron absorbing sheets 74 and a pair of tubular neutron source cavities 76 within which a pair of neutron sources 78 may be selectively positioned. The proportion of thermal neutrons that enter the activation region 34 can be adjusted by moving the pair of neutron sources 78 between position A, where the pair of neutron absorbing sheets 74 are respectively interposed directly between the pair of neutron sources 78 and the activation region 34, and position B, where the pair of neutron absorbing sheets 74 are not respectively interposed directly between the pair of neutron sources 78 and the activation region 34 whereby the proportion of thermal neutrons that enter the activation region 34 is less when the neutron sources 78 are disposed at position A than when the neutron sources are disposed at position B. In an alternative embodiment (not shown), additional neutron absorbing sheets having a different degree of neutron absorption than the neutron absorbing sheets 74 are disposed in those positions that are directly between the respective neutron sources 78 and the activation region 34 when the respective neutron sources are disposed in position B. In other respects the embodiment of FIGS. 6A and 6B is the same as the embodiment of FIG. 2.

In an alternative embodiment (not shown), the proportion of thermal neutrons that enter the activation region 34 is adjusted by adjusting the distance beneath the activation region 34 at which the neutron sources 14 and their surrounding gamma-ray shield 18 are disposed, whereby there is more or less neutron moderator 20 between the neutron sources 14 and the activation region 34 to thereby adjust the degree to which the velocity of the neutrons emitted from the neutron sources 14 is decreased. In other alternative embodiments (not shown), the proportion of thermal neutrons that enter the activation region 34 is adjusted by adjusting the degree of neutron moderation provided by the neutron moderator 20 disposed between the neutron sources 14 and the activation region 34, such as by adjusting the quantity of neutron moderator 20 disposed between the neutron sources 14 and the activation region 34 and/or by varying the neutron moderating material included in the neutron moderator 20.

Figure 7:
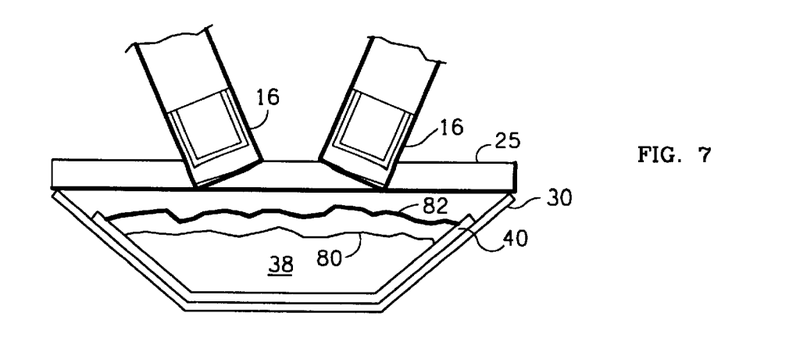
FIG. 7 is a diagram of a further alternative preferred embodiment of the portion of the bulk material analyzer adjacent the activation region, as viewed in the direction of the conveyor belt, in which an adjustable depth of the bulk material on a conveyor belt is shown.

FIG. 7 illustrates a further alternative preferred embodiment in which the depth of the bulk material on a conveyor belt 40 is adjusted between the depth shown as 80 to the depth shown as 82 in order to adjust the disposition of the bulk material 38 in the activation region 34. The change in the depth of the bulk material on the conveyor belt 40 is adjusted by (a) varying the speed of the conveyor belt 40, onto which the bulk material 38 is being fed at a relatively constant rate; (b) varying the rate at which the bulk material 38 is fed onto the conveyor belt 40 while the speed of the conveyor belt is relatively constant or (c) varying both the speed of the conveyor belt 40 and the rate at which the bulk material 38 is fed onto the conveyor belt 40. By adjusting the depth of the bulk material 38 on the conveyor belt 40 to the greater depth 82, the sensitivity of the detectors 16 to the top portion of the bulk material 38 on the conveyor belt 40 is increased by reason of the closer proximity of the top portion of the bulk material 38 to the detectors 16, while the sensitivity of the detectors 16 to the lower portion of the bulk material 38 on the conveyor belt 40 is decreased by reason of greater attenuation of gamma rays by the increased quantity of the intervening bulk material 38. If the top of the bulk material 38 is within a range of 2.5 to 7.5 centimeters from a detector 16, the effect of moving the top of the bulk material 38 closer to the detector 16 is greater than the loss of thermal-neutron flux, thereby increasing the sensitivity to the top portion of the bulk material 38. However if the Hydrogen content of the bulk material is too high, one cannot increase sensitivity to the top portion of the bulk material 38 sufficiently to overcome the loss of thermal-neutron flux by merely increasing the depth of the bulk material. In such an event, the technique of increasing the depth of the bulk material is combined with the technique of reducing the proportion of thermal neutrons that enter the activation region 34 from the lower side of the activation region 34 and/or the technique of increasing the quantity of neutrons that are reflected into the activation region 34 from the upper side of the activation region 34.

Other alternative preferred embodiments (not shown) include various combinations of the neutron absorbers, the neutron reflectors, the other means for adjusting the proportion of thermal neutrons that enter the activation region and the means for adjusting the depth of the bulk material on the conveyor belt described above.

In one preferred embodiment of the method of the present invention, the uniformity of sensitivity of the bulk material analyzer to materials at different positions in a sample of bulk material 38 on a conveyor belt 40 is enhanced by the step of (a) adjusting the proportion of thermal neutrons that enter the activation region 34 from the lower side of the activation region in combination with one or more of the steps of (b) adjusting the quantity of neutrons that enter the activation region 34 from the upper side of the activation region 34; and (c) adjusting the disposition of the bulk material sample 38 in the activation region 34, all as separately described above.

In another preferred embodiment of the method of the present invention that is performed specifically for enhancing analysis by the bulk material analyzer of a batch of bulk material 38 when the bulk material analyzer has not been adjusted to be uniformly sensitive to material at different positions in the samples of bulk material 38 being analyzed, such as when the bulk material is known to have a substantially different Hydrogen content that the bulk material previously analyzed or when it is determined that the bulk material analyzer has not been adjusted for the bulk material being analyzed, the uniformity of sensitivity of the bulk material analyzer to materials at different positions in such sample of bulk material 38 is enhanced by at least one of the steps of (a) adjusting the proportion of thermal neutrons that enter the activation region 34 from the lower side of the activation region 34; (b) adjusting the quantity of neutrons that enter the activation region 34 from the upper side of the activation region 34; and (c) adjusting the disposition of the bulk material sample 38 in the activation region 34, all as separately described above, and preferably is enhanced by a combination of a plurality of said steps. The amount of Hydrogen content in a sample of bulk material 38 can be determined by the use of a $He_3$ detector just above the top of the bulk material 38 on the conveyor belt 40. The $He_3$ detector is usually wrapped with a neutron absorber so that only epithermal neutrons are detected. The number of epithermal neutrons reaching the $He_3$ detector provides a good measure of the moisture in the batch of bulk material 38being analyzed.

The present invention is particularly useful for analyzing bulk materials 38 that are fed onto the conveyor belt 40 in layers of different bulk materials often having different moisture/Hydrogen contents, such as when a layer of clay is fed on top of a layer of limestone, which typically has a substantially lower moisture/Hydrogen content than clay.

The respective thicknesses of the neutron moderator 20, the neutron absorbers 23, 54, 58, 74 and the neutron reflectors 25, 70, 72 are determined for an activation region 34 of given dimensions and a bulk material samples 38 of a given depths and profiles by computer-aided modeling in accordance the Monte Carlo technique described in the above-referenced manual entitled "MCNP—A General Monte Carlo Code for Neutron and Photon Transport". For a bulk material analyzer having an activation region of a given geometry, several models are prepared in advance for various combinations of moisture content and depth of bulk material 38 on the conveyor belt 40 for different types of bulk material and layers of different combinations of bulk material so that adjustments can readily be made for the batch of bulk material being analyzed. For a plurality of layers of different bulk materials, one determines the sensitivity of each layer in comparison to the other layers and by systematically changing parameters such as the thickness of the neutron moderator, the location and thickness of the neutron absorber, the depth of the bulk material on the belt and the neutron reflector position and thickness, one may optimize the design for uniformity of sensitivity throughout the thickness of the bulk material sample on the conveyor belt.

An example of a process of adjusting the sensitivity within samples of bulk material having two layers of different materials is as follows:

(a) Using the Monte-Carlo technique a computer-aided model is provided for a representation of the bulk material analyzer apparatus and geometry and the bulk material being analyzed.

(b) A separate count is recorded for the prompt-neutron-activation gamma-rays reaching the detector(s) from each layer. This count is normalized to the mass of the layer. The measure of sensitivity of the layer is the number of gamma-ray counts reaching the detector(s) per neutrons emitted from the source, divided by the mass of the layer. The sensitivity is measured in units of counts/kg/neutron).

(c) The control parameters of neutron moderator thickness, neutron absorber location and thickness, depth of the bulk material on the belt and neutron reflector position and thickness are varied in a controlled manner and the ratio of the sensitivity of the layers as determined by the Monte Carlo technique is recorded. By varying these control parameters the ratios of the sensitivities are made to be as close to I as practical.

(d) The moisture (or total Hydrogen) content of the material being measured is then varied to determine the change in the sensitivity ratio as a function of total moisture/Hydrogen in the material being measured. This also is done using the Monte Carlo technique.

(e) Based upon the changes in sensitivity observed by varying the above control parameters, one adjusts one or more of these parameters so as to approximately cancel out the change in the sensitivity ratio as a function of the moisture content.

(f) Alternative to step (e), the Monte Carlo technique is used to optimize the system by adjusting the above control parameters to optimal values for several different moisture (or total Hydrogen content) levels. Although this step is more arduous means, it is also more precise.

This adjustment process can be done on-line. However, it is more practical to determine the correction required for moisture (total Hydrogen) content beforehand in accordance with step (e) or (f). It is also possible to make experimental measurements beforehand to determine such correction but this is much more difficult than using the Monte-Carlo technique.

This adjustment process may be generalized for more than two layers in the bulk material being analyzed. One method of making a multi-layer correction is to plot the sensitivity as a function of depth for about ten layers and to adjust the control parameters in order to make the sensitivity-versus-depth characteristic as uniform as possible.

It is particularly important to adjust the sensitivity to be reasonably uniform in the vertical direction when there are layered bulk materials on the conveyor belt. If the materials in the layers have a different composition then if the average sensitivity for one layer is different than the average sensitivity for the other layer, whereby absent such an adjustment the measured chemical composition will be biased toward the layer with the higher average sensitivity.

The above-described features of the present invention also are incorporated in bulk material analyzers in which the bulk material is transported through the activation region by a chute (not shown).

The advantages specifically stated herein do not necessarily apply to every conceivable embodiment of the present invention. Further, such stated advantages of the present invention are only examples and should not be construed as the only advantages of the present invention.

While the above description contains many specificities, these should not be construed as limitations on the scope of the present invention, but rather as examples of the preferred embodiments described herein. Other variations are possible and the scope of the present invention should be determined not by the embodiments described herein but rather by the claims and their legal equivalents.

We claim:

1. A bulk material analyzer in which bulk material is received in an activation region between at least one neutron source and at least one gamma-ray detector, comprising a container having surfaces defining the activation region; and at least one neutron source disposed within the container on one side of the activation region for emitting neutrons that enter the activation region for bombarding bulk material within the activation region to cause gamma-rays to be emitted from said bombarded bulk material;

at least one gamma-ray detector disposed within the container on another side of the activation region opposite from the one side of the activation region for detecting gamma-rays emitted from said bombarded bulk material;

a neutron moderator disposed between the at least one neutron source and the activation region for reducing the velocity of said emitted neutrons such that the neutrons entering the activation region include thermal neutrons and faster neutrons; and a neutron absorber disposed close to the one side of the activation region for reducing the proportion of thermal neutrons that enter the activation region from the one side of the activation region.

2. A bulk material analyzer according to claim 1, wherein the neutron absorber is disposed between the activation region and at least almost all of the neutron moderator that is disposed between the at least one neutron source and the activation region.

3. A bulk material analyzer according to claim 1, wherein the neutron absorber is disposed in a conveyor belt.

4. A bulk material analyzer according to claim 1, wherein the neutron absorber is adjustable for adjusting the proportion of thermal neutrons that enter the activation region from the one side of the activation region.

5. A bulk material analyzer according to claim 1, wherein disposition of the at least one neutron source is adjustable for adjusting the proportion of thermal neutrons that enter the activation region from the one side of the activation region.

6. A bulk material analyzer according to claim 1, further comprising neutron reflector means disposed on the other side of the activation region for reflecting neutrons into the activation region for bombarding bulk material within the activation region to cause gamma-rays to be emitted from said bombarded bulk material, wherein the neutron reflector means is adjustable for adjusting the quantity of neutrons that enter the activation region from the other side of the activation region.

7. A bulk material analyzer according to claim 1, further comprising neutron reflector means disposed on the other side of the activation region and at least as close to the other side of the activation region as the at least one gamma-ray detector for reflecting neutrons into the activation region for bombarding bulk material within the activation region to cause gamma-rays to be emitted from said bombarded bulk material.

8. A bulk material analyzer according to claim 1 for analyzing bulk material that is transported through the activation region on a conveyor belt, wherein the container surfaces further define a passageway for enabling bulk material to be transported through the activation region by the conveyor belt.

9. A bulk material analyzer according to claim 1 for analyzing bulk material that is transported through the activation region on a conveyor belt having upwardly and outwardly extended sides, wherein the container surfaces further define a passageway for enabling bulk material to be transported through the activation region by the conveyor belt, with a lower portion of the passageway-defining surfaces defining a trough having upwardly and outwardly extended sides adjacent the activation region for cradling the conveyor belt.

10. A method of enhancing uniformity of sensitivity of a bulk material analyzer to materials at different positions in a sample of bulk material received in an activation region between at least one neutron source disposed on one side of the activation region for emitting neutrons that enter the activation region for bombarding bulk material within the activation region to cause gamma-rays to be emitted from said bombarded bulk material, and at least one gamma-ray detector disposed on another side of the activation region opposite from the one side of the activation region for detecting gamma-rays emitted from said bombarded bulk material, wherein the bulk material analyzer includes a neutron moderator disposed between the at least one neutron source and the activation region for reducing the velocity of said emitted neutrons such that the neutrons entering the activation region include thermal neutrons and faster neutrons, the method comprising the step of:

(a) adjusting the proportion of thermal neutrons that enter the activation region from the one side of the activation region.

11. A method according to claim 10, wherein step (a) comprises the step of:

(b) disposing a neutron absorber close to the one side of the activation region to reduce the proportion of thermal neutrons that enter the activation region from the one side of the activation region.

12. A method according to claim 11, wherein step (a) further comprises the step of:

(c) adjusting the neutron absorber to adjust the proportion of thermal neutrons that enter the activation region from the one side of the activation region.

13. A method according to claim 11, wherein step (a) further comprises the step of:

(c) adjusting the disposition of the at least one neutron source.

14. A method according to claim 10, wherein step (a) comprises the step of:

(b) adjusting the disposition of the at least one neutron source.

15. A method according to claim 10, further comprising the step of:

(b) adjusting the quantity of neutrons that enter the activation region from another side of the activation region opposite from the one side of the activation region.

16. A method according to claim 15, further comprising the step of (c) adjusting the disposition of the bulk material sample in the activation region.

17. A method according to claim 10, further comprising the step of:

(b) adjusting the disposition of the bulk material sample in the activation region.

18. A method according to claim 17 for use when the bulk material sample is supported in the activation region, wherein step (b) comprises the step of:

(c) adjusting the depth of the bulk material sample.

19. A method of enhancing uniformity of sensitivity of a bulk material analyzer to materials at different positions in a sample of bulk material received in an activation region between at least one neutron source disposed on one side of the activation region for emitting neutrons that enter the activation region for bombarding bulk material within the activation region to cause gamma-rays to be emitted from said bombarded bulk material, and at least one gamma-ray detector disposed on another side of the activation region opposite from the one side of the activation region for detecting gamma-rays emitted from said bombarded bulk material, wherein the bulk material analyzer includes a neutron moderator disposed between the at least one neutron source and the activation region for reducing the velocity of said emitted neutrons such that the neutrons entering the activation region include thermal neutrons and faster neutrons, the method being performed specifically for enhancing analysis by the bulk material analyzer of a batch of bulk material when the bulk material analyzer has not been adjusted to be uniformly sensitive to material at different positions in the samples of bulk material being analyzed and comprising at least one of the following steps:

(a) adjusting the proportion of thermal neutrons that enter the activation region from the one side of the activation region; and (b) adjusting the quantity of neutrons that enter the activation region from the other side of the activation region.

20. A method according to claim 19, comprising steps (a) and (b).

21. A method according to claim 19, comprising step (a) and the step of adjusting the disposition of the bulk material sample in the activation region.

22. A method according to claim 19, comprising step (b) and the step of adjusting the disposition of the bulk material sample in the activation region.

23. A method according to claim 19, comprising steps (a), (b) and the step of adjusting the disposition of the bulk material sample in the activation region.

* * * * *